(12) United States Patent
Rao et al.

(10) Patent No.: US 8,214,224 B2
(45) Date of Patent: Jul. 3, 2012

(54) PATIENT DATA MINING FOR QUALITY ADHERENCE

(75) Inventors: R. Bharat Rao, Berwyn, PA (US); Sathyakama Sandilya, Cranbury, NJ (US); Harm J. Scherpbier, Fort Washington, PA (US); Thomas R. Warrick, Wayne, PA (US)

(73) Assignees: Siemens Medical Solutions USA, Inc., Malvern, PA (US); Siemens Corporation, Iselin, NJ (US)

( * ) Notice: Subject to any disclaimer, the term of this patent is extended or adjusted under 35 U.S.C. 154(b) by 2189 days.

(21) Appl. No.: 10/287,074

(22) Filed: Nov. 4, 2002

(65) Prior Publication Data

US 2003/0125985 A1 Jul. 3, 2003

Related U.S. Application Data

(60) Provisional application No. 60/335,542, filed on Nov. 2, 2001.

(51) Int. Cl.
*G06Q 10/00* (2006.01)
*G06Q 50/00* (2006.01)

(52) U.S. Cl. ............................................. 705/2; 705/3

(58) Field of Classification Search .................. 705/2–3
See application file for complete search history.

(56) References Cited

U.S. PATENT DOCUMENTS

| | | |
|---|---|---|
| 4,946,679 A | 8/1990 | Thys-Jacobs |
| 5,172,418 A | 12/1992 | Ito et al. |
| 5,307,262 A | 4/1994 | Ertel |
| 5,359,509 A | 10/1994 | Little et al. |
| 5,365,425 A | 11/1994 | Torma et al. |
| 5,508,912 A | 4/1996 | Schneiderman |
| 5,544,044 A | 8/1996 | Leatherman |
| 5,557,514 A | 9/1996 | Seare et al. |
| 5,619,991 A | 4/1997 | Sloane |
| 5,652,842 A | 7/1997 | Siegrist, Jr. et al. |
| 5,657,255 A | 8/1997 | Fink et al. |
| 5,664,109 A | 9/1997 | Johnson et al. |
| 5,669,877 A | 9/1997 | Blomquist |
| 5,706,441 A | 1/1998 | Lockwood |

(Continued)

FOREIGN PATENT DOCUMENTS

DE 198 20 276 11/1999

(Continued)

OTHER PUBLICATIONS

"Machine Learning and Data Mining", Mitchell, Communications of the ACM, Nov. 1999, ACM, USA, Onlinel, vol. 42, No. 11, Nov. 1999, pp. 30-36, retrieved from internet: http://portal.acm.org/ft_gateway.cfm?.

(Continued)

*Primary Examiner* — Sheetal R Rangrej
(74) *Attorney, Agent, or Firm* — Joshua Ryan (57) ABSTRACT

The present invention provides systems and methods for automatically ensuring adherence to clinical guidelines during the course of patient treatments. A data source contains patient records, including records for patients being treated; a guidelines knowledge base contains clinical guidelines; and a quality adherence engine is configured to monitor adherence with the clinical guidelines for patients being treated. At least some of the patient records may include information obtained from mining unstructured patient data. The system includes an output component for outputting quality adherence information. The outputted quality adherence information may include reminders, including reminders to take clinical actions in accordance with the clinical guidelines. The outputted quality adherence information may also include warnings that the clinical guidelines have not been observed.

32 Claims, 4 Drawing Sheets

U.S. PATENT DOCUMENTS

| | | | |
|---|---|---|---|
| 5,724,379 A | 3/1998 | Perkins et al. | |
| 5,724,573 A | 3/1998 | Agrawal et al. | |
| 5,737,539 A | 4/1998 | Edelson et al. | |
| 5,738,102 A | 4/1998 | Lemelson | 128/671 |
| 5,811,437 A | 9/1998 | Singh et al. | |
| 5,832,450 A | 11/1998 | Myers et al. | |
| 5,835,897 A | 11/1998 | Dang | |
| 5,845,253 A | 12/1998 | Rensimer et al. | |
| 5,899,998 A | 5/1999 | McGauley et al. | |
| 5,903,889 A * | 5/1999 | de la Huerga et al. | 1/1 |
| 5,908,383 A | 6/1999 | Brynjestad | 600/300 |
| 5,924,073 A | 7/1999 | Tyuluman et al. | |
| 5,924,074 A * | 7/1999 | Evans | 705/3 |
| 5,935,060 A | 8/1999 | Iliff | |
| 5,939,528 A | 8/1999 | Clardy et al. | |
| 5,991,731 A | 11/1999 | Colon et al. | |
| 6,039,688 A * | 3/2000 | Douglas et al. | 600/300 |
| 6,067,466 A | 5/2000 | Selker et al. | |
| 6,076,088 A | 6/2000 | Paik et al. | |
| 6,078,894 A | 6/2000 | Clawson et al. | |
| 6,081,786 A | 6/2000 | Barry et al. | |
| 6,083,693 A | 7/2000 | Nandabalan et al. | |
| 6,108,635 A | 8/2000 | Herren et al. | |
| 6,125,194 A | 9/2000 | Yeh et al. | |
| 6,128,620 A | 10/2000 | Pissanos et al. | |
| 6,139,494 A | 10/2000 | Cairnes | 600/300 |
| 6,151,581 A | 11/2000 | Kraftson et al. | |
| 6,173,280 B1 | 1/2001 | Ramkumar et al. | |
| 6,196,970 B1 | 3/2001 | Brown | |
| 6,212,519 B1 | 4/2001 | Segal | |
| 6,212,526 B1 | 4/2001 | Chaudhuri et al. | |
| 6,253,186 B1 | 6/2001 | Pendleton, Jr. | |
| 6,259,890 B1 | 7/2001 | Driscoll et al. | |
| 6,266,645 B1 | 7/2001 | Simpson | |
| 6,272,472 B1 | 8/2001 | Danneels et al. | |
| 6,322,502 B1 | 11/2001 | Schoenberg et al. | |
| 6,322,504 B1 | 11/2001 | Kirshner | |
| 6,338,042 B1 | 1/2002 | Paizis | |
| 6,381,576 B1 | 4/2002 | Gilbert | |
| 6,468,210 B1 | 10/2002 | Iliff | |
| 6,478,737 B2 | 11/2002 | Bardy | |
| 6,484,144 B2 | 11/2002 | Martin et al. | |
| 6,523,019 B1 | 2/2003 | Borthwick | |
| 6,529,876 B1 | 3/2003 | Dart | |
| 6,551,243 B2 | 4/2003 | Bocionek et al. | |
| 6,551,266 B1 | 4/2003 | Davis, Jr. | |
| 6,587,829 B1 | 7/2003 | Camarda et al. | |
| 6,611,825 B1 | 8/2003 | Billheimer et al. | |
| 6,611,846 B1 | 8/2003 | Stoodley | |
| 6,641,532 B2 | 11/2003 | Iliff | |
| 6,645,959 B1 | 11/2003 | Bakker-Arkema et al. | |
| 6,678,669 B2 | 1/2004 | Lapointe et al. | |
| 6,754,655 B1 | 6/2004 | Segal | |
| 6,802,810 B2 | 10/2004 | Ciarniello et al. | |
| 6,804,656 B1 | 10/2004 | Rosenfeld et al. | |
| 6,826,536 B1 | 11/2004 | Forman | |
| 6,839,678 B1 | 1/2005 | Schmidt et al. | |
| 6,903,194 B1 | 6/2005 | Sato et al. | |
| 6,915,254 B1 | 7/2005 | Heinze et al. | |
| 6,915,266 B1 | 7/2005 | Saeed et al. | |
| 6,941,271 B1 | 9/2005 | Soong | |
| 6,961,687 B1 | 11/2005 | Myers, Jr. et al. | |
| 6,988,075 B1 | 1/2006 | Hacker | |
| 7,058,658 B2 | 6/2006 | Mentzer | |
| 7,130,457 B2 | 10/2006 | Kaufman et al. | |
| 7,249,006 B2 | 7/2007 | Lombardo et al. | |
| 7,307,543 B2 | 12/2007 | Rosenfeld et al. | |
| 7,353,238 B1 | 4/2008 | Gliklich | |
| 7,630,908 B1 | 12/2009 | Amrien et al. | |
| 2001/0011243 A1 | 8/2001 | Dembo et al. | |
| 2001/0023419 A1* | 9/2001 | Lapointe et al. | 706/15 |
| 2001/0032195 A1 | 10/2001 | Graichen et al. | |
| 2001/0041991 A1 | 11/2001 | Segal et al. | |
| 2001/0051882 A1 | 12/2001 | Murphy et al. | |
| 2002/0002474 A1 | 1/2002 | Michelson et al. | |
| 2002/0010597 A1* | 1/2002 | Mayer et al. | 705/2 |
| 2002/0026332 A1 | 2/2002 | Snowden et al. | |
| 2002/0032581 A1 | 3/2002 | Reitberg | |
| 2002/0035316 A1* | 3/2002 | Drazen | 600/300 |
| 2002/0038227 A1* | 3/2002 | Fey et al. | 705/3 |
| 2002/0077853 A1 | 6/2002 | Boru et al. | |
| 2002/0082480 A1 | 6/2002 | Riff et al. | |
| 2002/0087361 A1 | 7/2002 | Benigno et al. | |
| 2002/0099570 A1 | 7/2002 | Knight | |
| 2002/0123905 A1 | 9/2002 | Goodroe et al. | |
| 2002/0138492 A1 | 9/2002 | Kil | |
| 2002/0138524 A1 | 9/2002 | Ingle et al. | |
| 2002/0143577 A1 | 10/2002 | Shiffman et al. | |
| 2002/0165736 A1 | 11/2002 | Tolle et al. | |
| 2002/0173990 A1 | 11/2002 | Marasco | |
| 2002/0177759 A1 | 11/2002 | Schoenberg et al. | |
| 2003/0028401 A1 | 2/2003 | Kaufman et al. | |
| 2003/0046114 A1 | 3/2003 | Davies et al. | |
| 2003/0050794 A1 | 3/2003 | Keck | |
| 2003/0108938 A1 | 6/2003 | Pickar et al. | |
| 2003/0120133 A1 | 6/2003 | Rao et al. | |
| 2003/0120134 A1 | 6/2003 | Rao et al. | |
| 2003/0120458 A1 | 6/2003 | Rao et al. | |
| 2003/0120514 A1 | 6/2003 | Rao et al. | |
| 2003/0125984 A1 | 7/2003 | Rao et al. | |
| 2003/0125988 A1 | 7/2003 | Rao et al. | |
| 2003/0126101 A1 | 7/2003 | Rao et al. | |
| 2003/0130871 A1 | 7/2003 | Rao et al. | |
| 2003/0135391 A1 | 7/2003 | Edmundson et al. | |
| 2003/0208382 A1* | 11/2003 | Westfall | 705/3 |
| 2004/0078216 A1 | 4/2004 | Togo | |
| 2004/0184644 A1 | 9/2004 | Leichter et al. | |
| 2004/0243586 A1 | 12/2004 | Byers | |
| 2005/0187794 A1 | 8/2005 | Kimak | |
| 2005/0191716 A1 | 9/2005 | Surwit et al. | |
| 2006/0064415 A1 | 3/2006 | Guyon et al. | |
| 2006/0136259 A1 | 6/2006 | Weiner et al. | |

FOREIGN PATENT DOCUMENTS

| | | |
|---|---|---|
| EP | 0 596 247 A2 | 5/1994 |
| EP | 0 641 863 | 3/1995 |
| EP | 0 917 078 A1 | 10/1997 |
| GB | 2 332 544 A | 6/1999 |
| JP | 11328073 A | 11/1999 |
| JP | 2001297157 A | 10/2001 |
| WO | WO9829790 | 7/1998 |
| WO | 98/39720 | 9/1998 |
| WO | WO 00/51054 | 8/2000 |
| WO | WO 00/69331 | 11/2000 |
| WO | WO 01/66007 | 9/2001 |
| WO | WO 01/78005 A2 | 10/2001 |
| WO | 01/82173 A1 | 11/2001 |

OTHER PUBLICATIONS

"Data Mining for the Enterprise", Kleissner, System Sciences, 1998, Proceedings of the Thirty-First Hawaii International Conference on Kohala Coast. HI, USA Jan. 6-9, 1998, Los Alamitos, CA, USA, IEEE Comput. Soc. US, Jan. 6, 1998, pp. 295-304.

"Improved Diagnostic end Prognostic Assessments Using Health Management Information Fusion", Roemer et al., 20001 IEEE Autotestcon Proceedings, IEEE Systems Readiness Technology Conference. Autotestcon 2001. vol. CONF. 37, Aug. 20, 2001,pp. 385-377.

"Data Mining for Disease Management: Adding Value to Patient Records", Rao et al., Electromedla, Online!, vol. 68, 2000, pp. 63-67, retrieved from the internet: http://www.med.siemens.com/medroot/en/news/electro/issues/pdf/onco_2000_e/9.pdf.

"Information Understanding Integrating Data Fusion and Data Mining Processes", Waltz et al, Circuits and Systems, 1998, ISCAS 98, Proceedings of the 1998 IEEE International Symposium on Monterey, CA, USA May 31-Jun. 3, 1998, NY, NY, USA, IEEE, May 31, 1998, pp. 553-556.

"A Mutually Beneficial Integration of Data Mining and Information Extraction", Nahm et al., Proceedings AAAI, National Conference on Artificial Intelligence, Jul. 30, 2000, pp. 627-632.

"Using Data Mining to Characterize DNA Mutations by Patient Clinical Features", Evans et al., 1997 AMIA Annual Fall Symposium, Proceedings of 1997 AMIA Annual Fall Symposium the Emergence of Internetable Health Care Systems That Really Work, Nashville, TN, pp. 253-257.

"The Colorectal Cancer Recurrence Support (CARES) System", Ong et al., Artificial Intelligence in Medicine, Nov. 1997, Elsevier, Netherlands, vol. 11, No. 3, pp. 175-188.

"Database System Support for Multidimensional Data Analysis in Environmental Epidemiology", Kemp et al., Database Engineering and Applications Symposium, 1997, Ideas 97, Proceedings, International Montreal, Clue, Canada, Aug. 25-27, 1997, Los Alamitos, CA, USA, IEEE Comput. Soc., US, pp. 180-188.

Mills, "Computer Technology of the Not-too-distant Future", Sep. 1993, Medical Laboratory Observer, vol. 25, No. 9, p. 78.

Duda, "Pattern Classification", 2001, John Wiley & Sons, Inc., p. vii-xx, Chapter 1.

Hudson, "The feasibility of using automated data to assess guideline-concordant care for schizophrenia", Dec. 4, 1999, Journal of Medical Systems, vol. 23, No. 4, pp, 299-307.

PR Newsire, Diabetes Health Management Award Honors Mayor Clinic's Zimmerman, Sep. 25, 2000.

Hudson, "CAATS and compliance", Apr. 1998, The Internal Auditor, vol. 55, No. 2, p. 25.

Hofer, "The Unreliability of Individual Physician "Report Cards" for Assessing the Costs and Quality of Care of a Chronic Disease", Jun. 9, 1999, JAMA, vol. 281, No. 22:2098-2105.

King et al., MEDUS/A: Distributing Database Management for Medical Research, Proceedings of Computer Networks Compcon 82, Sep. 20-23, 1982, pp. 635-642.

Boxwala et al., "Architecture for a Multipurpose Guideline Execution Engine", Proc. AMIA Symp 1999, pp. 701-705.

Guidance for Institutional Review Boards and Clinical Investigators 1998 Update, Sep. 1998, U.S. Food and Drug Administration.

Kassirer, "The Use and Abuse of Practice Profiles", Mar. 3, 1994, The New England Journal of Medicine, vol. 330:634-636.

Chen, "Do "America's Best Hospitals" Perform Better for Acute Myocardial Infarctions?", Jan. 28, 1999, The New England Journal of Medicine, vol. 340, No. 4:286-292.

Dato, et al., The Nation's Current Capacity for the Early Detection of Public Health Threats Including Bioterrorism, Agency for Healthcare Research and Quality, Jun. 8, 2001.

Hanson, et al., Bayesian Classification Theory, Technical Report FIA-90-12-7-01, 1991, pp. 1-10.

Diadoo, Cindy A., An Assessment for the Need of a Bioterrorism Preparedness Plan at Hospital XYZ in Minnesota, The Graduate College, University of Wisconsin-Stout, Dec. 1999, pp. 1-57.

Wagner, et al., Availability and Comparative Value of Data Elements Required for an Effective Bioterrorisnn Detection System, Nov. 28, 2001, Agency for Healthcare Research and Quality, pp. 1-184.

Bregg, et al., Assessment of Diagnostic Tests When Disease is Subject to Selection Bias, Biometrics, vol. 39, No. 1, Mar. 1983, pp. 207-215.

Grimes, "Structure, Models and Meaning, is "Unstructured" Data Merely Unmodeled?", Mar. 1, 2005, Intelligent Enterprise, http://www.intelligententerprise.com/showArticte.jhtml?articleID=59301538.

Berkus, "Unstructured Data" as an Oxymoron, Sep. 1, 2005, ITtoolbox Blogs, http://blogs.ittoolbox.com/database/soup/archives/unstructured-data-as-an-oxymoron-5588.

Larsen, "Fast and effective text mining using linear-time document clustering", 1999, ACM Press, Conference on Knowledge Discovery in Data, Proceedings of the fifth ACM SIGKDD International Conference on Knowledge Discovery and Data Mining, pp. 16-22.

Rao, "From Unstructured Data to Actionable Intelligence", IT Pro, Nov./Dec. 2003, pp, 29-35.

* cited by examiner

PATIENT DATA MINING FOR QUALITY ADHERENCE

CROSS REFERENCE TO RELATED APPLICATIONS

This application claims the benefit of U.S. Provisional Application Ser. No. 60/335,542, filed on Nov. 2, 2001, which is incorporated by reference herein in its entirety.

FIELD OF THE INVENTION

The present invention relates to medical information processing systems, and, more particularly to a computerized system and method for providing quality adherence information for health care organizations.

BACKGROUND OF THE INVENTION

Health care organizations are increasingly turning to evidence-based approaches to improve quality of care. For instance, health care organizations typically employ clinical guidelines that provide recommendations based on the best available medical scientific evidence. Health care quality can be measured by comparing clinical actions to guideline recommendations.

The results of such comparisons can be used by health care organizations to determine areas of excellence within their organizations as well as those areas that need improvement. This information provides an objective basis for planning and making budgeting decisions. In addition, it may be used to demonstrate accountability to the public and back up claims of quality.

Currently, solutions that address the issue of quality of care usually only focus on retrospective comparisons with clinical guidelines. Although retrospective comparisons can provide valuable information, there are generally few mechanisms in place for ensuring adherence to guidelines during the course of patient treatment. Such information would be very useful in determining problems as they happen, so that corrective action could immediately be taken.

As health care organizations migrate toward environments where most aspects of patient care management are automated, it is now easier to collect and analyze patient information. However, health care organizations tend to maintain information in a myriad of unstructured and structured data sources. For example, it may be necessary to access numerous different databases, each with its own peculiar format. Worse, physician notes may have to be consulted. These notes usually are nothing more than free text dictations, and it may be very difficult to sift through the notes to gather the necessary information. As a result, the effort taken to collect information is usually time consuming, expensive, and error prone.

Given the importance of providing quality of care information, it would be desirable and highly advantageous to generate accurate quality adherence information during the course of patient treatment.

SUMMARY OF THE INVENTION

The present invention provides a technique for generating accurate quality adherence information during the course of patient treatment.

In various embodiments of the present invention, a system is provided that includes a data source containing patient records, including records for patients being treated; a guidelines knowledge base containing clinical guidelines; and a quality adherence engine for monitoring adherence with the clinical guidelines for the patients being treated. At least some of the patient records may include information obtained from mining unstructured patient data.

The system includes an output component for outputting quality adherence information. The outputted quality adherence information may include reminders, including reminders to take clinical actions in accordance with the clinical guidelines. The outputted quality adherence information may also include warnings that the clinical guidelines have not been observed.

The quality adherence engine may be configured to monitor adherence to the clinical guidelines by comparing clinical actions with clinical guidelines. The clinical guidelines can relate to recommended clinical actions. The quality adherence engine can monitor adherence to the clinical guidelines by determining the next recommended clinical actions. Reminders for the next recommended clinical actions can be output so that health care providers are better able to follow the recommendations.

These and other aspects, features and advantages of the present invention will become apparent from the following detailed description of preferred embodiments, which is to be read in connection with the accompanying drawings.

DESCRIPTION OF PREFERRED EMBODIMENTS

To facilitate a clear understanding of the present invention, illustrative examples are provided herein which describe certain aspects of the invention. However, it is to be appreciated that these illustrations are not meant to limit the scope of the invention, and are provided herein to illustrate certain concepts associated with the invention.

It is also to be understood that the present invention may be implemented in various forms of hardware, software, firmware, special purpose processors, or a combination thereof. Preferably, the present invention is implemented in software as a program tangibly embodied on a program storage device. The program may be uploaded to, and executed by, a machine comprising any suitable architecture. Preferably, the machine is implemented on a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the program (or combination thereof) which is executed via the operating system. In addition, various other peripheral devices may be connected to the computer platform such as an additional data storage device and a printing device.

It is to be understood that, because some of the constituent system components and method steps depicted in the accompanying figures are preferably implemented in software, the actual connections between the system components (or the process steps) may differ depending upon the manner in which the present invention is programmed.

Figure 1:
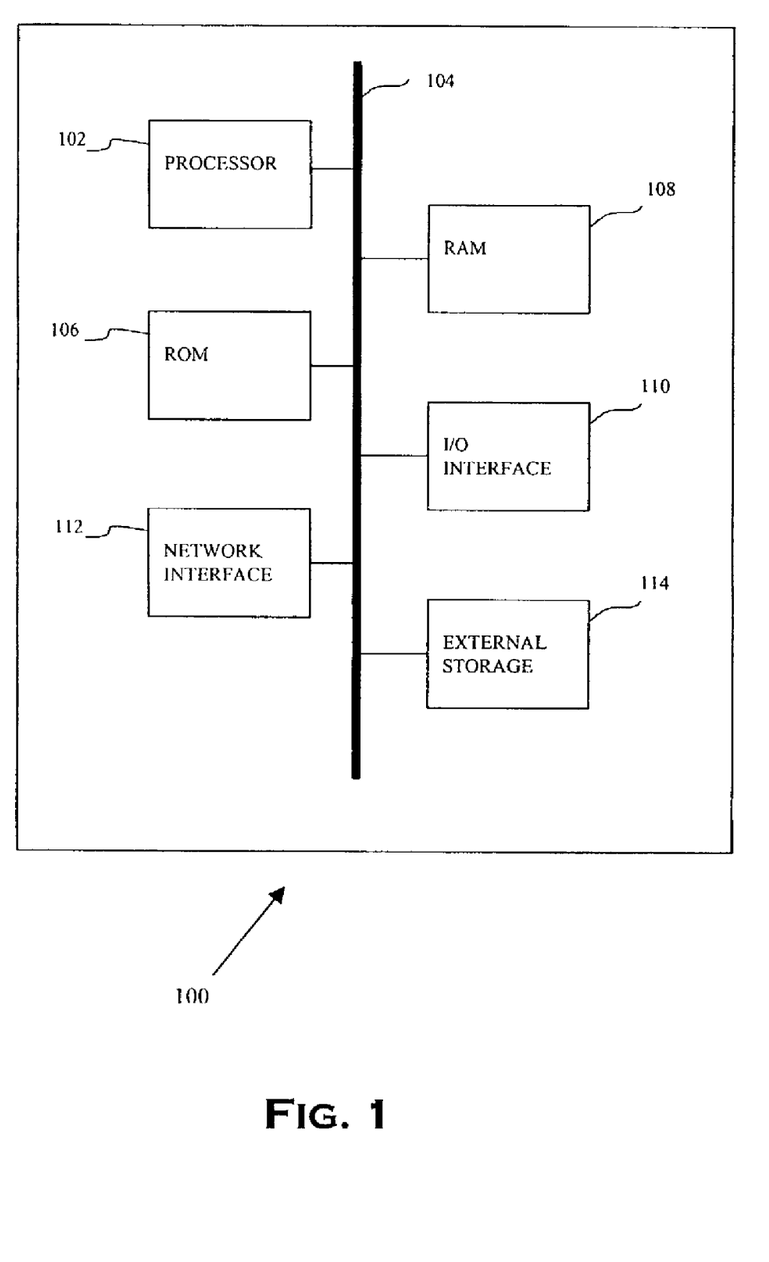
FIG. 1 is a block diagram of a computer processing system to which the present invention may be applied according to an embodiment of the present invention.

FIG. 1 is a block diagram of a computer processing system 100 to which the present invention may be applied according to an embodiment of the present invention. The system 100 includes at least one processor (hereinafter processor) 102 operatively coupled to other components via a system bus 104. A read-only memory (ROM) 106, a random access memory (RAM) 108, an I/O interface 110, a network interface 112, and external storage 114 are operatively coupled to the system bus 104. Various peripheral devices such as, for example, a display device, a disk storage device (e.g., a magnetic or optical disk storage device), a keyboard, and a mouse, may be operatively coupled to the system bus 104 by the I/O interface 110 or the network interface 112.

The computer system 100 may be a standalone system or be linked to a network via the network interface 112. The network interface 112 may be a hard-wired interface. However, in various exemplary embodiments, the network interface 112 can include any device suitable to transmit information to and from another device, such as a universal asynchronous receiver/transmitter (UART), a parallel digital interface, a software interface or any combination of known or later developed software and hardware. The network interface may be linked to various types of networks, including a local area network (LAN), a wide area network (WAN), an intranet, a virtual private network (VPN), and the Internet.

The external storage 114 may be implemented using a database management system (DBMS) managed by the processor 102 and residing on a memory such as a hard disk. However, it should be appreciated that the external storage 114 may be implemented on one or more additional computer systems. For example, the external storage 114 may include a data warehouse system residing on a separate computer system.

Those skilled in the art will appreciate that other alternative computing environments may be used without departing from the spirit and scope of the present invention.

Figure 2:
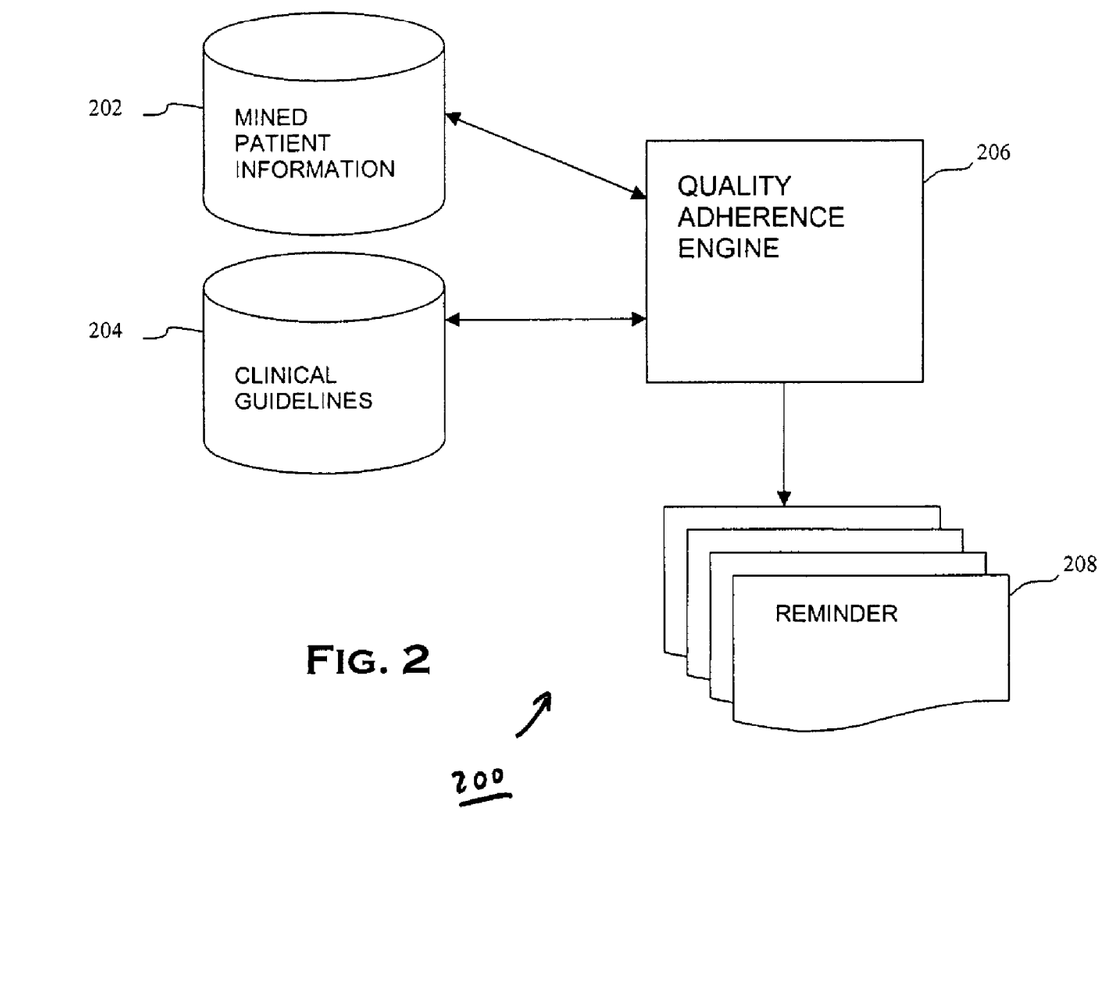
FIG. 2 shows an exemplary quality assurance system in accordance with an embodiment of the present invention.

Referring to FIG. 2, an automated quality adherence system 200 is illustrated. The automated quality adherence system 200 includes a data source 202 containing patient records, a clinical guidelines knowledge base 204, a quality adherence engine 206, and an output component 208. The automated quality adherence system 200 is configured to monitor adherence with clinical guidelines for patients being treated.

Preferably, the data source 202 is organized as a structured clinical patient record (CPR) and populated with patient information using data mining techniques described in "Patient Data Mining," by Rao et al., copending U.S. patent application Ser. No. 10/287,055, published as 2003-0120458, filed herewith, which is incorporated by reference herein in its entirety.

Figure 3:
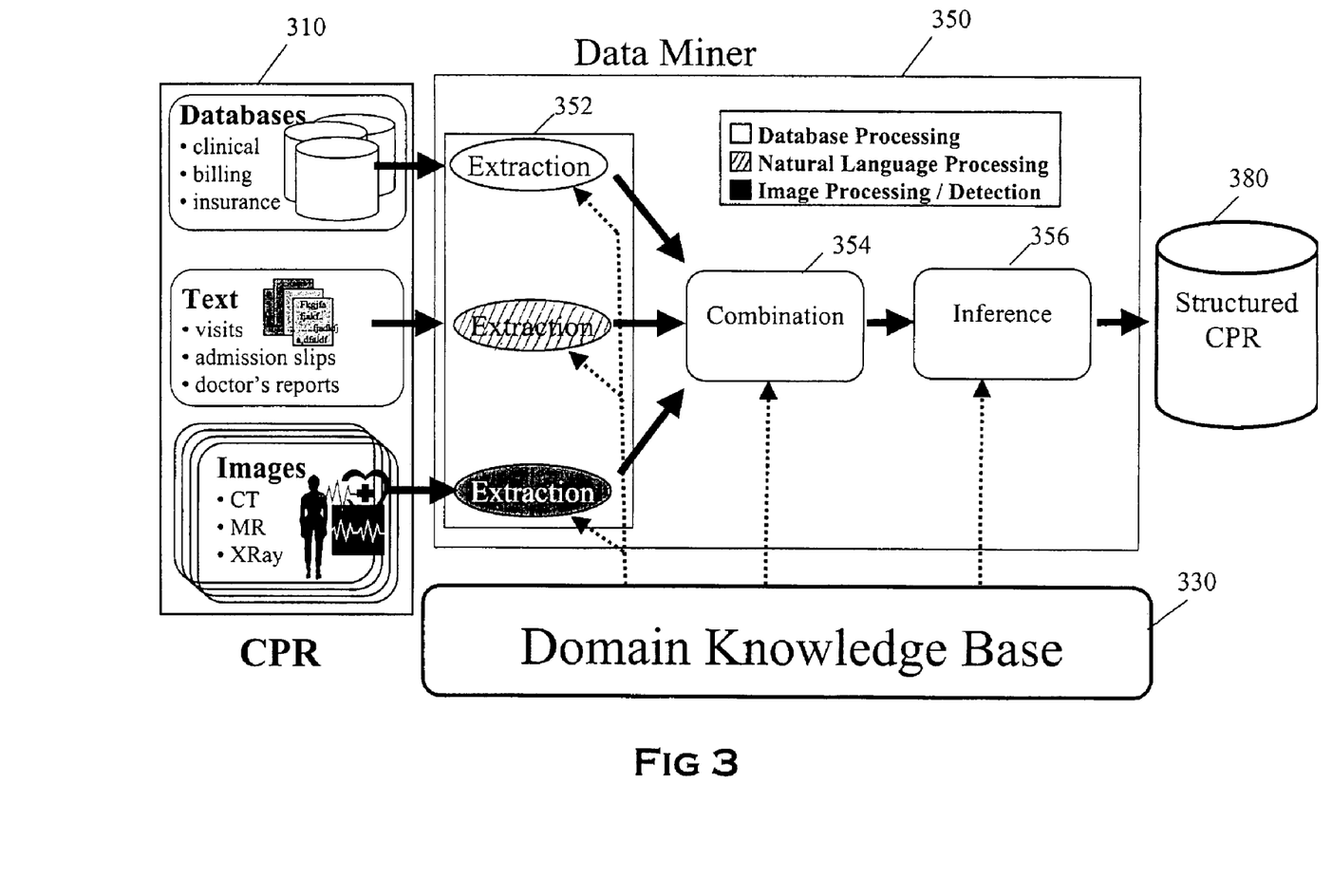
FIG. 3 shows an exemplary data mining framework for mining structured clinical information.

As illustrates in FIG. 3, an exemplary data mining framework for mining high-quality structured clinical information includes a data miner 350 that mines information from a CPR 310 using domain-specific knowledge contained in a knowledge base 330. The data miner 350 includes components for extracting information from the CPR 352, combining all available evidence in a principled fashion over time 354, and drawing inferences from this combination process 356. The mined information may be stored in a structured CPR 380.

The extraction component 352 deals with gleaning small pieces of information from each data source regarding a patient, which are represented as probabilistic assertions about the patient at a particular time. These probabilistic assertions are called elements. The combination component 354 combines all the elements that refer to the same variable at the same time period to form one unified probabilistic assertion regarding that variable. These unified probabilistic assertions are called factoids. The inference component 356 deals with the combination of these factoids, at the same point in time and/or at different points in time, to produce a coherent and concise picture of the progression of the patient's state over time. This progression of the patient's state is called a state sequence.

An individual model of the state of a patient may be built. The patient state is simply a collection of variables that one may care about relating to the patient. The information of interest may include a state sequence, i.e., the value of the patient state at different points in time during the patient's treatment.

Each of the above components uses detailed knowledge regarding the domain of interest, such as, for example, a disease of interest. This domain knowledge base (330) can come in two forms. It can be encoded as an input to the system, or as programs that produce information that can be understood by the system. The part of the domain knowledge base (330) that is input to the present form of the system may also be learned from data.

Domain-specific knowledge for mining the data sources may include institution-specific domain knowledge. For example, this may include information about the data available at a particular hospital, document structures at a hospital, policies of a hospital, guidelines of a hospital, and any variations of a hospital.

The domain-specific knowledge may also include disease-specific domain knowledge. For example, the disease-specific domain knowledge may include various factors that influence risk of a disease, disease progression information, complications information, outcomes and variables related to a disease, measurements related to a disease, and policies and guidelines established by medical bodies.

As mentioned, the extraction component (352) takes information from the CPR (310) to produce probabilistic assertions (elements) about the patient that are relevant to an instant in time or time period. This process is carried out with the guidance of the domain knowledge that is contained in the domain knowledge base (330). The domain knowledge required for extraction is generally specific to each source.

Extraction from a text source may be carried out by phrase spotting, which requires a list of rules that specify the phrases of interest and the inferences that can be drawn therefrom. For example, if there is a statement in a doctor's note with the words "There is evidence of metastatic cancer in the liver," then, in order to infer from this sentence that the patient has cancer, a rule is needed that directs the system to look for the phrase "metastatic cancer," and, if it is found, to assert that the patient has cancer with a high degree of confidence (which, in the present embodiment, translates to generate an element with name "Cancer", value "True" and confidence 0.9).

The data sources include structured and unstructured information. Structured information may be converted into standardized units, where appropriate. Unstructured information may include ASCII text strings, image information in DICOM (Digital Imaging and Communication in Medicine) format, and text documents partitioned based on domain knowledge. Information that is likely to be incorrect or missing may be noted, so that action may be taken. For example, the mined information may include corrected information, including corrected ICD-9 diagnosis codes.

Extraction from a database source may be carried out by querying a table in the source, in which case, the domain knowledge needs to encode what information is present in which fields in the database. On the other hand, the extraction process may involve computing a complicated function of the information contained in the database, in which case, the domain knowledge may be provided in the form of a program that performs this computation whose output may be fed to the rest of the system.

Extraction from images, waveforms, etc., may be carried out by image processing or feature extraction programs that are provided to the system.

Combination includes the process of producing a unified view of each variable at a given point in time from potentially conflicting assertions from the same/different sources. In various embodiments, this is performed using domain knowledge regarding the statistics of the variables represented by the elements ("prior probabilities").

Inference is the process of taking all the factoids that are available about a patient and producing a composite view of the patient's progress through disease states, treatment protocols, laboratory tests, etc. Essentially, a patient's current state can be influenced by a previous state and any new composite observations.

The domain knowledge required for this process may be a statistical model that describes the general pattern of the evolution of the disease of interest across the entire patient population and the relationships between the patient's disease and the variables that may be observed (lab test results, doctor's notes, etc.). A summary of the patient may be produced that is believed to be the most consistent with the information contained in the factoids, and the domain knowledge.

For instance, if observations seem to state that a cancer patient is receiving chemotherapy while he or she does not have cancerous growth, whereas the domain knowledge states that chemotherapy is given only when the patient has cancer, then the system may decide either: (1) the patient does not have cancer and is not receiving chemotherapy (that is, the observation is probably incorrect), or (2) the patient has cancer and is receiving chemotherapy (the initial inference—that the patient does not have cancer—is incorrect); depending on which of these propositions is more likely given all the other information. Actually, both (1) and (2) may be concluded, but with different probabilities.

As another example, consider the situation where a statement such as "The patient has metastatic cancer" is found in a doctor's note, and it is concluded from that statement that <cancer=True (probability=0.9)>. (Note that this is equivalent to asserting that <cancer=True (probability:0.9), cancer=unknown (probability=0.1)>).

Now, further assume that there is a base probability of cancer <cancer=True (probability=0.35), cancer=False (probability=0.65)> (e.g., 35% of patients have cancer). Then, we could combine this assertion with the base probability of cancer to obtain, for example, the assertion <cancer=True (probability=0.93), cancer=False (probability=0.07)>.

Similarly, assume conflicting evidence indicated the following:
1. <cancer=True (probability=0.9), cancer=unknown probability=0.1)>
2. <cancer=False (probability=0.7), cancer=unknown (probability=0.3)>
3. <cancer=True (probability=0.1), cancer=unknown (probability=0.9)> and
4. <cancer=False (probability=0.4), cancer=unknown (probability=0.6)>.

In this case, we might combine these elements with the base probability of cancer <cancer=True (probability=0.35), cancer=False (probability=0.65)> to conclude, for example, that <cancer=True (prob=0.67), cancer=False (prob=0.33)>.

Numerous data sources may be accessed, and missing, incorrect, and/or inconsistent information may be dealt with. As an example, consider that, in determining whether a patient has diabetes, the following information might have to be extracted:

(a) ICD-9 billing codes for secondary diagnoses associated with diabetes;

(b) drugs administered to the patient that are associated with the treatment of diabetes (e.g., insulin);

(c) patient's lab values that are diagnostic of diabetes (e.g., two successive blood sugar readings over 250 mg/d);

(d) doctor mentions that the patient is a diabetic in the H&P (history & physical) or discharge note (free text); and (e) patient procedures (e.g., foot exam) associated with being a diabetic.

As can be seen, there are multiple independent sources of information, observations from which can support (with varying degrees of certainty) that the patient is diabetic (or more generally has some disease/condition). Not all of them may be present, and in fact, in some cases, they may contradict each other. Probabilistic observations can be derived, with varying degrees of confidence. Then these observations (e.g., about the billing codes, the drugs, the lab tests, etc.) may be probabilistically combined to come up with a final probability of diabetes. Note that there may be information in the patient record that contradicts diabetes. For instance, the patient is has some stressful episode (e.g., an operation) and his blood sugar does not go up.

It should be appreciated that the above examples are presented for illustrative purposes only and are not meant to be limiting. The actual manner in which elements are combined depends on the particular domain under consideration as well as the needs of the users of the system. Further, it should be appreciated that while the above discussion refers to a patient-centered approach, actual implementations may be extended to handle multiple patients simultaneously. Additionally, it should be appreciated that a learning process may be incorporated into the domain knowledge base (330) for any or all of the stages (i.e., extraction, combination, inference).

Referring again to FIG. 2, the automated quality adherence system 200 can be configured to output quality adherence information, such as, for example reminders. The reminders may be generated to prompt physicians to take clinical actions in accordance with the clinical guidelines. The outputted quality adherence information may also include warnings that the clinical guidelines have not been observed.

The patient records contained in the data source 202 may include information regarding clinical actions taken during patient treatments. For example, the patient records may contain information regarding various tests and procedures administered to the patient.

The quality adherence engine 206 may be configured to monitor adherence to clinical guidelines by comparing clinical actions with the clinical guidelines. Since the clinical action information may be a product of inferences, it may therefore be probabilistic in nature. Thus, the warnings may be generated if there is a likelihood that the guidelines haven't been followed. Probability values may be assigned to each clinical action, and warnings issued if the probability that the guidelines weren't followed exceeds a predefined threshold.

The quality adherence engine 206 may also monitor adherence to clinical guidelines by determining the next recommended clinical actions. Reminders for the next recommended clinical actions may be output so that health care personnel are better able to follow the recommendations.

For example, guidelines for treatment of acute myocardial infarction (AMI) promulgated by the Joint Commission on Accreditation of Healthcare Organizations (JCAHO) call for certain AMI patients without aspirin contraindication to receive aspirin within 24 hours before or after hospital arrival. In this case, the quality adherence engine 206 can select patient records for AMI patients from the data source 202, and generate a reminder that aspirin should be given to certain of those patients. If the 24 hour period expired without aspirin being provided to an AMI patient, then a warning may instead be outputted.

The output component 208 may output these reminders and warnings, as the case may be, along with other quality adherence information. The output component 208 may be implemented to output this information via a printed report, a computer display device, etc. However, in various other embodiments, the quality adherence information may be integrated into a physician calendar/scheduling system.

Figure 4:
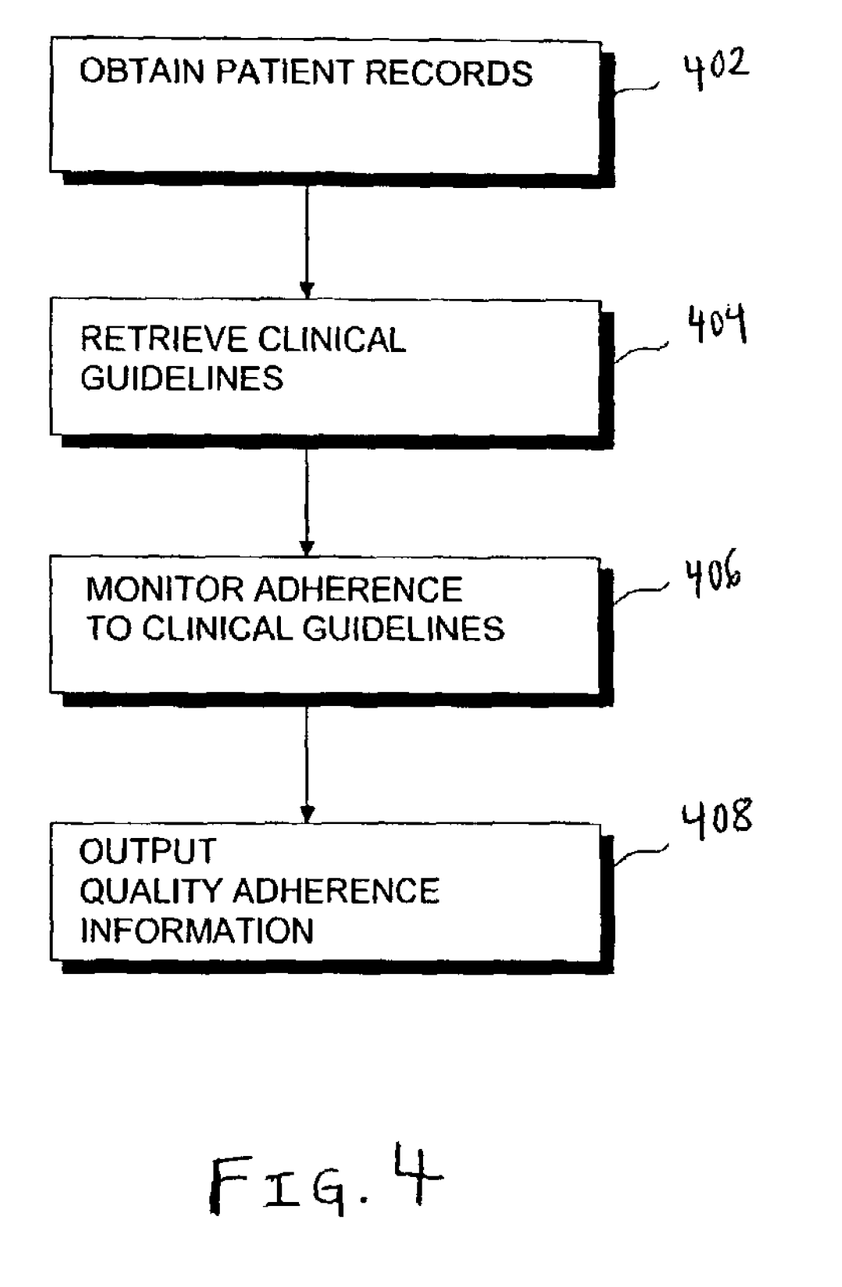
FIG. 4 shows a flow diagram outlining an exemplary technique for automatically ensuring adherence to clinical guidelines during the course of patient treatments.

Referring to FIG. 4, a flow diagram outlining an exemplary technique for automatically ensuring adherence to clinical guidelines during the course of patient treatments is illustrated. Beginning at step 402, patient records are obtained from a data source. At least some of the obtained patient records may contain treatment information derived from unstructured information, such as, for example, physician notes, medical images, and waveform information. Preferably, this information resides in a structured data repository populated using mined unstructured patient information, as described in "Patient Data Mining," by Rao et al., copending U.S. patent application Ser. No. 10/287,055, published as 2003-0120458.

In step 404, clinical guidelines are retrieved from a clinical guidelines knowledge base. For example, the clinical guidelines may be stored in a database, and contain recommended clinical actions for various diseases of interest. These clinical guidelines may include recommendations promulgated by accreditation organizations (such as JCAHO), government agencies, and consumer health care organizations. In addition, clinical guidelines may be created for internal use (e.g., by a hospital to measure quality of care). In general, clinical guidelines may include any list of recommended clinical actions.

Next, in step 406, adherence to the clinical guidelines are monitored. This may involve determining the current patient diagnosis, and comparing clinical actions taken with respect to the patient to relevant guidelines. If recommended clinical actions were not observed, warnings may be generated to physicians and other medical personnel. The recommended next clinical actions for the patient may also be determined, and reminders may be generated.

In step 408, quality adherence information, such as the reminders and warnings, may be output via a report, a computer display, or even integrated into a calendar or scheduling system.

As shown in FIGS. 1-4, this invention is preferably implemented using a general purpose computer system. However the systems and methods of this invention can be implemented using any combination of one or more programmed general purpose computers, programmed microprocessors or micro-controllers and peripheral integrated circuit elements, ASIC or other integrated circuits, digital signal processors, hardwired electronic or logic circuits such as discrete element circuits, programmable logic devices such as a PLD, PLA, FPGA or PAL, or the like.

Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A system for automatically ensuring adherence to clinical guidelines, comprising:
    a data source containing at least one patient record, including a first record for a patient being treated, the first patient record including structured information mined from unstructured patient data by a processor, the unstructured patient data including free text, the structured information for the patient being treated comprising values for variables related to clinical actions for the patient being treated, each of the values inferred from pieces extracted, by mining, from the unstructured patient data for the patient being treated, the pieces for each variable assigned respective first probabilities of indicating respective possible values, different pieces indicating different possible values of the respective variable, a plurality of the first probabilities referring to a same one of the variables combined into a unified probability for the value for the same one of the variables, at least one of the first probabilities being less than 100%, the value for the same one of the variables determined from the unified probability, the pieces and possible values for each of the variables being for the patient being treated, at least one of the pieces extracted from the free text;
    a guideline knowledge base containing a clinical guideline; and
    a quality adherence engine for monitoring adherence with the clinical guideline as a function of the information mined from unstructured patient data in the first record for the patient being treated.

2. The system of claim 1, further including an output component for outputting quality adherence information.

3. The system of claim 2, wherein the outputted quality adherence information includes reminders.

4. The system of claim 3, wherein the reminders include reminders to take a clinical action in accordance with the clinical guidelines.

5. The system of claim 2, wherein the outputted quality adherence information includes warnings that the clinical guideline has not been observed.

6. The system of claim 2, wherein the outputted quality adherence information includes warning that the clinical guideline has not been observed based on a probability exceeding a threshold.

7. The system of claim 2 wherein the outputted quality adherence information includes a report.

8. The system of claim 2 wherein the outputted quality adherence information includes schedule information.

9. The system of claim 1, wherein the at least one patient record comprises a plurality of patient records, the patient records contained in the data source include information regarding the clinical actions taken during patient treatments.

10. The system of claim 9, wherein the quality adherence engine monitors adherence to the clinical guideline at least in part by comparing the clinical action with the clinical guideline.

11. The system of claim 10, wherein the clinical guideline relate to recommended clinical action.

12. The system of claim 11, wherein the quality adherence engine monitors adherence to the clinical guideline at least in part by determining a subsequent recommended clinical action.

13. The system of claim 12, wherein the quality adherence engine monitors adherence to the clinical guideline at least in part by outputting a reminder for the subsequent recommended clinical action.

14. The system of claim 1 wherein the quality adherence engine is operable to identify a relevant guideline for the patient being treated.

15. The system of claim 1 wherein the quality adherence engine is operable to assign a probability to each of a plurality of clinical actions.

16. The system of claim 1 wherein the clinical guideline comprises health care person performed actions and the adherence comprises evaluation of compliance by the health care person.

17. A method for automatically ensuring adherence to clinical guidelines during the course of patient treatments, the method comprising the steps of:
obtaining a patient record for a patient being treated, the patient record containing at least some structured information from a mined unstructured data source, the structured information comprising values for variables related to clinical actions for the patient being treated, the values for the variables inferred from pieces extracted, by processor mining, from the unstructured patient data source, the pieces for each variable assigned respective first probabilities for different possible values for the respective variable, a plurality of the first probabilities referring to a same one of the variables of the patient being treated combined into a unified probability for the value for the same one of the variables, at least one of the first probabilities being less than 100%, the value determined from the unified probability, the pieces and possible values being for the patient being treated, at least one of the pieces extracted from free text;
retrieving a clinical guideline from a guideline knowledge base; and
monitoring adherence to the clinical guideline for the patient being treated as a function of the information from the mined unstructured data source.

18. The method of claim 17, further including the step of outputting quality adherence information.

19. The method of claim 18, wherein the outputted quality adherence information includes a reminder.

20. The method of claim 19, wherein the reminder is to take a clinical action in accordance with the clinical guideline.

21. The method of claim 18, wherein the outputted quality adherence information includes a warning that the clinical guideline has not been observed.

22. The method of claim 18, wherein the outputted quality adherence information includes a warning that the clinical guideline has not been observed based on a probability exceeding a threshold.

23. The method of claim 18, wherein the obtained patient record includes the clinical action taken during a patient treatment.

24. The method of claim 23, wherein monitoring adherence to the clinical guideline includes comparing the clinical action with the clinical guideline.

25. The method of claim 24, wherein the clinical guideline relates to a recommended clinical action.

26. The method of claim 24, wherein monitoring adherence to the clinical guideline further includes determining a subsequent recommended clinical action.

27. The method of claim 26, wherein monitoring adherence to the clinical guideline further includes outputting a reminder for the subsequent recommended clinical action.

28. A program storage device readable by a machine, tangibly embodying a program of instructions executable on the machine to perform method steps for automatically ensuring adherence to clinical guidelines, the method steps comprising:
obtaining patient records for patients being treated, at least some of the patient records containing information from mined unstructured data sources, the information for a first patient being treated comprising values for variables related to clinical actions, each of the values being from pieces extracted, by mining, from the unstructured patient data, each of the pieces for a same variable assigned first probabilities, a plurality of the first probabilities referring to the same one of the variables combined into a unified probability for the value for the same one of the variables, at least one of the first probabilities being less than 100%, the value determined from the unified probability, the pieces and values being for the patient being treated, at least one of the pieces extracted from free text of the unstructured data source;
retrieving clinical guidelines from a guidelines knowledge base; and
monitoring adherence to the clinical guidelines for the patients being treated as a function of the information from a mined unstructured data source.

29. The method of claim 18 wherein outputting comprises outputting a report.

30. The method of claim 18 wherein outputting comprises outputting schedule information.

31. The method of claim 17 wherein retrieving comprises identifying a relevant guideline for the patient being treated.

32. The method of claim 17 wherein monitoring comprises assigning a second probability to each of a plurality of clinical actions.

* * * * *